United States Patent
O'Dea

(10) Patent No.: US 9,439,633 B2
(45) Date of Patent: Sep. 13, 2016

(54) DEVICE AND A METHOD FOR FACILITATING MONITORING THE CROSS-SECTION OF A GASTRIC SLEEVE DURING FORMATION THEREOF

(75) Inventor: John O'Dea, Bearna (IE)

(73) Assignee: Flip Technologies Limited, Dangan (IE)

(*) Notice: Subject to any disclaimer, the term of this patent is extended or adjusted under 35 U.S.C. 154(b) by 118 days.

(21) Appl. No.: 13/500,640

(22) PCT Filed: Oct. 11, 2010

(86) PCT No.: PCT/IE2010/000056
§ 371 (c)(1),
(2), (4) Date: Jun. 27, 2012

(87) PCT Pub. No.: WO2011/042893
PCT Pub. Date: Apr. 14, 2011

(65) Prior Publication Data
US 2012/0277525 A1 Nov. 1, 2012

(30) Foreign Application Priority Data
Oct. 9, 2009 (IE) .................... S2009/0784

(51) Int. Cl.
*A61B 1/04* (2006.01)
*A61B 17/00* (2006.01)
(Continued)

(52) U.S. Cl.
CPC ....... *A61B 17/00234* (2013.01); *A61B 5/0538* (2013.01); *A61B 5/1076* (2013.01);
(Continued)

(58) Field of Classification Search
CPC .......... A61B 1/00082; A61B 1/00142; A61B 2017/22054; A61B 2018/00261; A61B 25/1011; A61B 5/1076; A61F 5/0003; A61F 5/003; A61F 5/0036; A61F 5/0073; A61F 5/0076; A61F 5/0079; A61F 5/0083; A61M 2210/1042; A61M 2210/1053; A61M 2210/1057; A61M 2210/106; A61M 25/1002
USPC ................... 600/115, 116; 604/95.03, 96.01, 604/101.01, 101.05, 103.07
See application file for complete search history.

(56) References Cited

U.S. PATENT DOCUMENTS 4,134,405 A * 1/1979 Smit ............................. 606/108
4,470,407 A 9/1984 Hussein
(Continued)

FOREIGN PATENT DOCUMENTS

EP 1654975 A1 5/2006
WO 2009/001325 A1 12/2008
(Continued)

OTHER PUBLICATIONS

International Search Report for PCT/IE2010/000056 dated Jan. 26 2011.

*Primary Examiner* — Anhtuan T Nguyen
*Assistant Examiner* — Jae Woo
(74) *Attorney, Agent, or Firm* — Sughrue Mion, PLLC

(57) ABSTRACT

A device (1) for monitoring the transverse cross-section of a gastric sleeve (3) as the gastric sleeve (3) is being formed in a stomach (4) during a sleeve gastrectomy procedure comprises a catheter (15) with a primary balloon (19) located thereon towards a distal end (17). The primary balloon (19) is located in the stomach, and the portion of the stomach which is to form the gastric sleeve (3) is stretched around the primary balloon (19) when the primary balloon (19) has been inflated to a diameter approximating to the diameter to which the sleeve (3) is to be formed. As the stomach (4) is being sutured to form the sleeve (3) the pressure within the primary balloon (19) is monitored to avoid excessive stretching of the stomach around the primary balloon (19). The diameter of the primary balloon (19) is also monitored to avoid necking of the sleeve (3) during suturing of the stomach (4).

15 Claims, 6 Drawing Sheets

Figure 1:
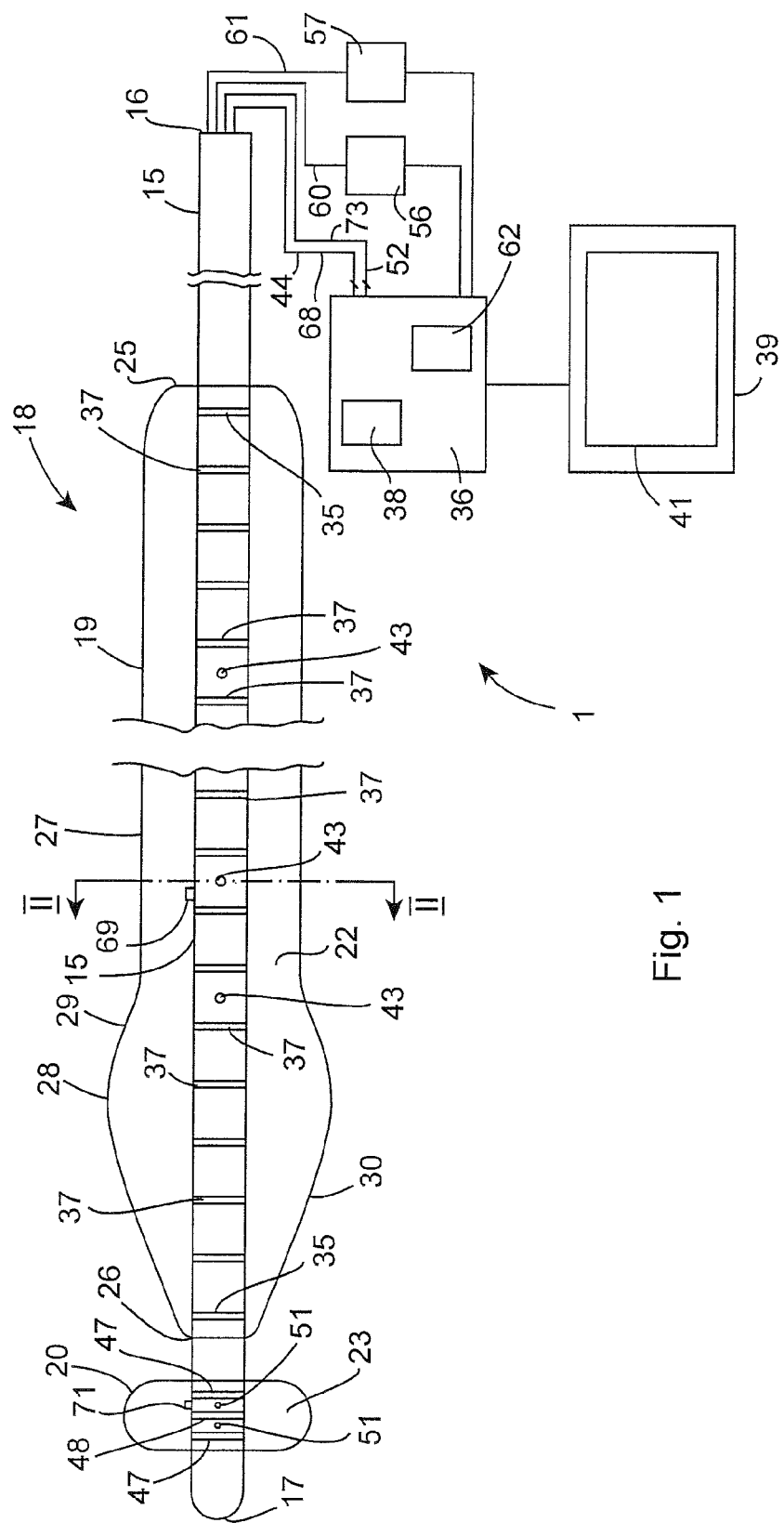

(51) Int. Cl.
*A61B 5/053* (2006.01)
*A61B 5/107* (2006.01)
*A61B 5/00* (2006.01)
*A61B 1/273* (2006.01)
*A61B 17/11* (2006.01)
*A61B 17/22* (2006.01)
*A61F 5/00* (2006.01)
*A61M 25/10* (2013.01)

(52) U.S. Cl.
CPC ........... *A61B5/4238* (2013.01); *A61B 5/6853* (2013.01); *A61M 25/1018* (2013.01); *A61B 1/2736* (2013.01); *A61B 17/1114* (2013.01); *A61B 2017/0003* (2013.01); *A61B 2017/00278* (2013.01); *A61B 2017/00292* (2013.01); *A61B 2017/00818* (2013.01); *A61B 2017/22054* (2013.01); *A61F 5/0076* (2013.01); *A61M 25/1002* (2013.01); *A61M 25/1011* (2013.01); *A61M 2210/1053* (2013.01)

(56) References Cited

U.S. PATENT DOCUMENTS

| | | | | |
|---|---|---|---|---|
| 4,573,966 A * | 3/1986 | Weikl et al. | | 604/509 |
| 5,234,454 A * | 8/1993 | Bangs | | A61F 5/003 |
| | | | | 604/101.05 |
| 5,273,536 A * | 12/1993 | Savas | | A61M 25/104 |
| | | | | 604/103.07 |
| 5,295,958 A * | 3/1994 | Shturman | | A61B 17/22012 |
| | | | | 604/103.07 |
| 5,338,298 A * | 8/1994 | McIntyre | | A61M 25/1002 |
| | | | | 604/103.07 |
| 5,352,199 A * | 10/1994 | Tower | | A61M 29/02 |
| | | | | 604/103.07 |
| 5,401,241 A * | 3/1995 | Delany | | 604/43 |
| 6,143,015 A * | 11/2000 | Nobles | | 606/194 |
| 6,159,219 A * | 12/2000 | Ren | | A61F 2/958 |
| | | | | 604/103.06 |
| 6,280,412 B1 * | 8/2001 | Pederson, Jr. | | A61F 2/958 |
| | | | | 604/103.07 |
| 6,293,959 B1 * | 9/2001 | Miller | | A61F 2/958 |
| | | | | 604/103.07 |
| 6,647,984 B1 * | 11/2003 | O'Dea | | 128/207.16 |
| 6,712,806 B2 * | 3/2004 | St. Germain et al. | | 604/509 |
| 6,796,960 B2 * | 9/2004 | Cioanta et al. | | 604/103.01 |
| 6,808,524 B2 * | 10/2004 | Lopath et al. | | 606/27 |
| 6,843,251 B1 * | 1/2005 | Huerland | | A61B 17/42 |
| | | | | 128/845 |
| 6,988,987 B2 * | 1/2006 | Ishikawa et al. | | 600/114 |
| 7,189,229 B2 * | 3/2007 | Lopath et al. | | 606/27 |
| 7,335,210 B2 * | 2/2008 | Smit | | 606/108 |
| 7,703,459 B2 * | 4/2010 | Saadat et al. | | 128/898 |
| 7,740,609 B2 * | 6/2010 | Rowe | | A61M 25/1011 |
| | | | | 604/101.04 |
| 7,803,195 B2 * | 9/2010 | Levy et al. | | 623/23.68 |
| 8,087,413 B2 * | 1/2012 | Saadat et al. | | 128/898 |
| 8,475,489 B2 * | 7/2013 | Desai et al. | | 606/200 |
| 8,486,011 B2 * | 7/2013 | O'Dea et al. | | 604/99.03 |
| 8,521,249 B2 * | 8/2013 | O'Dea | | 600/373 |
| 8,523,884 B2 * | 9/2013 | Stam et al. | | 606/151 |
| 2003/0040804 A1 * | 2/2003 | Stack | | A61F 2/04 |
| | | | | 623/23.7 |
| 2004/0199155 A1 * | 10/2004 | Mollenauer | | 606/27 |
| 2004/0236414 A1 * | 11/2004 | Brar et al. | | 623/1.42 |
| 2005/0059965 A1 * | 3/2005 | Eberl | | A61B 18/1492 |
| | | | | 606/41 |
| 2005/0080444 A1 * | 4/2005 | Kraemer et al. | | 606/192 |
| 2005/0187609 A1 * | 8/2005 | Brar et al. | | 623/1.15 |
| 2005/0197530 A1 | 9/2005 | Wallace et al. | | |
| 2005/0209674 A1 * | 9/2005 | Kutscher et al. | | 623/1.11 |
| 2005/9251158 | 11/2005 | Saadat et al. | | |
| 2006/0020278 A1 * | 1/2006 | Burnett | | A61B 5/14539 |
| | | | | 606/153 |
| 2006/0116586 A1 * | 6/2006 | Sekiguchi et al. | | 600/470 |
| 2006/0271088 A1 * | 11/2006 | Alfrhan | | A61F 5/0043 |
| | | | | 606/192 |
| 2007/0032702 A1 * | 2/2007 | Ortiz | | 600/205 |
| 2007/0060932 A1 * | 3/2007 | Stack et al. | | 606/153 |
| 2007/0100368 A1 * | 5/2007 | Quijano | | A61F 5/003 |
| | | | | 606/192 |
| 2007/0100369 A1 * | 5/2007 | Cragg | | A61F 5/003 |
| | | | | 606/192 |
| 2007/0106302 A1 * | 5/2007 | Ortiz | | 606/108 |
| 2007/0129735 A1 * | 6/2007 | Filipi et al. | | 606/144 |
| 2007/0250132 A1 * | 10/2007 | Burnett | | A61F 5/003 |
| | | | | 607/40 |
| 2008/0208239 A1 * | 8/2008 | Annunziata | | A61F 5/0079 |
| | | | | 606/191 |
| 2008/0249404 A1 * | 10/2008 | Mikkaichi | | A61B 17/00234 |
| | | | | 600/437 |
| 2009/0105735 A1 * | 4/2009 | Stam | | A61B 17/12 |
| | | | | 606/157 |
| 2009/0198266 A1 * | 8/2009 | Cesare | | 606/192 |
| 2009/0275942 A1 * | 11/2009 | Ortiz | | A61B 1/00165 |
| | | | | 606/50 |
| 2010/0094328 A1 * | 4/2010 | O'dea et al. | | 606/192 |
| 2010/0145324 A1 * | 6/2010 | Nihalani | | A61F 5/0013 |
| | | | | 606/14 |
| 2010/0228192 A1 * | 9/2010 | O'Dea et al. | | 604/104 |
| 2010/0228202 A1 * | 9/2010 | O'Dea et al. | | 604/264 |
| 2010/0305479 A1 * | 12/2010 | O'Dea | | 600/587 |
| 2011/0118650 A1 * | 5/2011 | Nihalani | | A61F 5/0076 |
| | | | | 604/9 |
| 2012/0035642 A1 * | 2/2012 | O'dea et al. | | 606/194 |
| 2012/0065571 A1 * | 3/2012 | Thompson | | A61F 5/0076 |
| | | | | 604/8 |
| 2012/0095384 A1 * | 4/2012 | Babkes | | A61F 5/0033 |
| | | | | 604/9 |
| 2013/0109906 A1 * | 5/2013 | Valoir | | A61N 5/1014 |
| | | | | 600/3 |
| 2014/0018722 A1 * | 1/2014 | Scott et al. | | 604/9 |

FOREIGN PATENT DOCUMENTS

| | | |
|---|---|---|
| WO | 2009/001327 A2 | 12/2008 |
| WO | 2009/001328 A2 | 12/2008 |
| WO | 2009/081387 A1 | 7/2009 |
| WO | 2009/097585 A1 | 8/2009 |

* cited by examiner

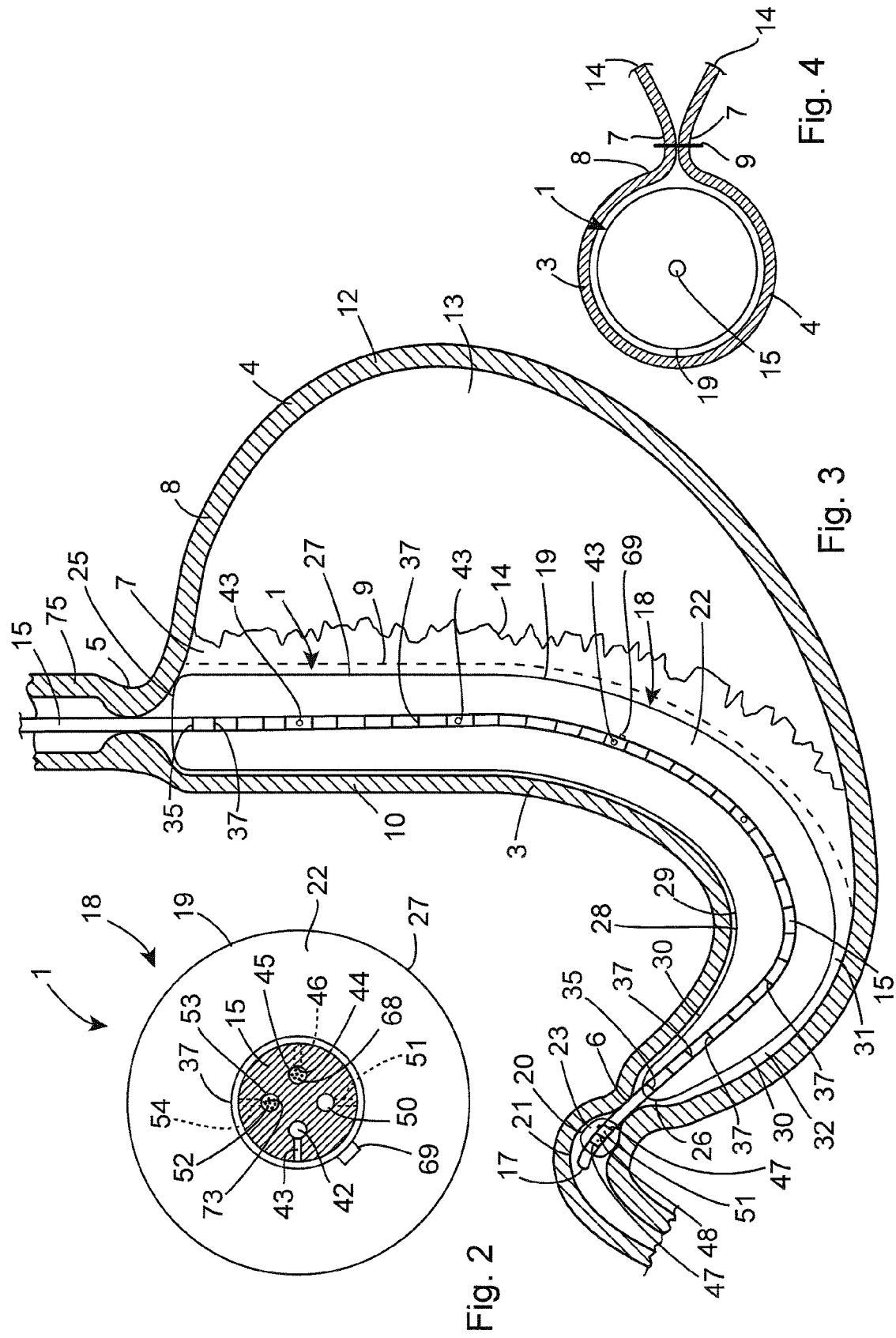

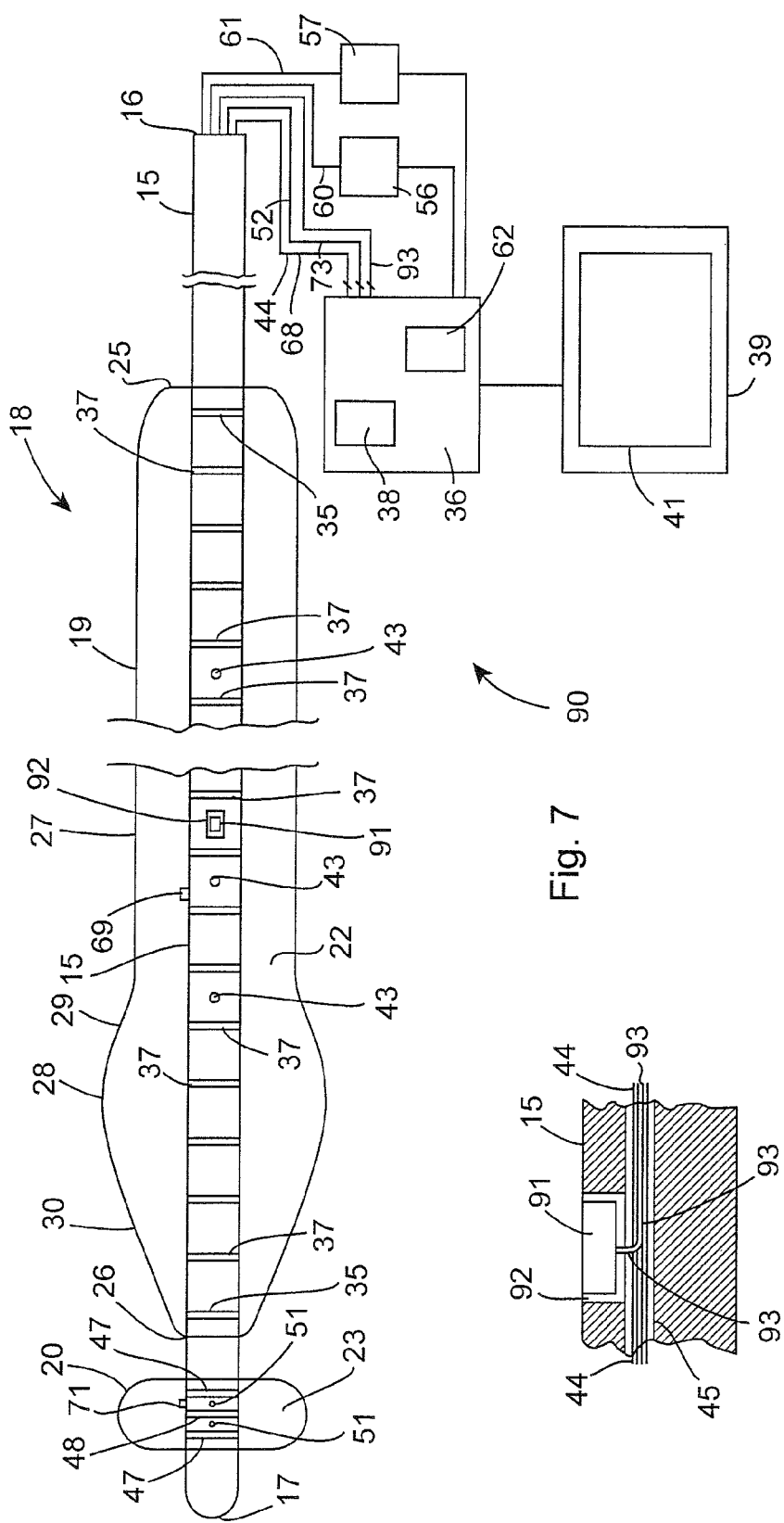

DEVICE AND A METHOD FOR FACILITATING MONITORING THE CROSS-SECTION OF A GASTRIC SLEEVE DURING FORMATION THEREOF

The present invention is directed towards a device for facilitating monitoring the transverse cross-section of a gastric sleeve during formation of the gastric sleeve from the stomach in a sleeve gastrectomy procedure, and the invention is also directed towards a method for monitoring the transverse cross-section of such a gastric sleeve during a sleeve gastrectomy.

The procedure known as a sleeve gastrectomy procedure whereby a gastric sleeve is formed from the stomach of a human or animal subject is a relatively new procedure, and is largely used to facilitate weight loss in a subject. The gastric sleeve is formed from the stomach and typically extends from the lower oesophageal sphincter to the pylorus, although the gastric sleeve may not necessarily extend to the pylorus. During the procedure to form the gastric sleeve, the stomach is sutured or stapled along a line which extends from the lower oesophageal sphincter to the pylorus or to the end of the sleeve remote from the lower oesophageal sphincter. The suturing or stapling line extends on respective opposite sides of the wall of the stomach in order to join opposite portions of the wall of the stomach to form the gastric sleeve. The suturing or stapling line is located closer to the lesser curvature side of the stomach which is to form a part of the gastric sleeve, than to the greater curvature side thereof, and is spaced apart from the side of lesser curvature which is to form the part of the gastric sleeve a distance between 11 mm and 20 mm. The remaining part of the stomach is then severed from the gastric sleeve and removed.

A problem which arises in the formation of such gastric sleeves is the difficulty of determining the precise location of the line along which the stomach is to be sutured or stapled in order to form the gastric sleeve of the desired cross-section. There is also a danger of the suturing or stapling line arcing inwardly towards the middle of the gastric sleeve, which can result in necking of the gastric sleeve intermediate the ends thereof, thereby leading to food blockages and other detrimental consequences.

There is therefore a need for a device and a method which addresses these problems.

The present invention is directed towards providing such a device and a method.

According to the invention there is provided a device for monitoring of the transverse cross-section of a gastric sleeve during formation thereof in a subject during a sleeve gastrectomy, the device comprising an elongated catheter extending between a proximal end and a distal end, a primary inflatable element defining a primary hollow interior region located on the catheter towards the distal end thereof, and a first communicating means communicating with the primary hollow interior region of the primary inflatable element for accommodating an inflating medium into the primary hollow interior region for inflating thereof, characterised in that the primary inflatable element when inflated is adapted to substantially define a desired transverse cross-section of the gastric sleeve.

In one embodiment of the invention, the primary inflatable element when inflated is adapted to substantially define the interior of the gastric sleeve.

In one embodiment of the invention the primary inflatable element is of a non-elastic material, and in an alternative embodiment of the invention the primary inflatable element is of an elastic material.

Preferably, the primary inflatable element defines a main portion extending from the proximal end thereof to a distal portion of greater transverse cross-section than the transverse cross-section of the main portion when the primary inflatable element is inflated. Advantageously, an intermediate portion of the primary inflatable element located between the distal portion and the main portion tapers proximally from the distal portion to the main portion when the primary inflatable element is inflated. Ideally, the primary inflatable element is adapted to extend through the stomach from the lower oesophageal sphincter, and advantageously, the primary inflatable element is adapted to extend into the antrum adjacent the pylorus, and the distal portion of the primary inflatable element is adapted for locating in the antrum.

In one embodiment of the invention, the distal portion of the primary inflatable element tapers distally towards the catheter when the primary inflatable element is inflated, and the distally tapering portion of the primary inflatable element is adapted for locating in the antrum. Preferably, the main portion of the primary inflatable element is of substantially constant transverse cross-sectional area when the primary inflatable element is inflated. Advantageously, the primary inflatable element is of circular transverse cross-section when inflated.

In another embodiment of the invention, the catheter extends through the primary inflatable element, and the primary inflatable element defines with the catheter an annular hollow interior region when inflated.

Preferably, a primary pressure sensing means is provided for monitoring the pressure of inflating medium in the primary inflatable element. Advantageously, the primary pressure sensing means is located in the catheter within the primary inflatable element.

In another embodiment of the invention at least one primary stimulating electrode is located in the primary hollow interior region on one of the catheter and an inner surface of the primary inflatable element for receiving a primary stimulating signal, and at least one primary sensing electrode is located within the primary hollow interior region on one of the catheter and an inner surface of the primary inflatable element axially spaced apart from the at least one primary stimulating electrode for producing a primary signal indicative of one of the transverse cross-sectional area and the diameter of the primary inflatable element in response to the primary stimulating signal when the primary inflatable element is inflated with an electrically conductive inflating medium.

Preferably, a pair of spaced apart primary stimulating electrodes are provided, and advantageously, a plurality of spaced apart primary sensing electrodes are provided between the primary stimulating electrodes and spaced apart therefrom.

Preferably, a second communicating means is provided for communicating with the primary stimulating and sensing electrodes.

In another embodiment of the invention the primary inflatable element is adapted to abut the pylorus on the proximal side thereof.

In a further embodiment of the invention a secondary inflatable element defining a secondary hollow interior region is located on the catheter spaced apart from the primary inflatable element and to one end of the primary inflatable element for to locating the catheter with the primary inflatable element located in the stomach.

In another embodiment of the invention, the secondary inflatable element is located distally of the primary inflatable element for engaging the duodenum with the pylorus located between the primary and secondary inflatable elements.

Preferably, the secondary inflatable element is distally spaced apart from the primary inflatable element a distance sufficient to accommodate the pylorus therebetween, and preferably, the secondary inflatable element is distally spaced apart from the primary inflatable element a distance in the range of 10 mm to 30 mm.

In another embodiment of the invention the secondary inflatable element is located proximally from the primary inflatable element, and advantageously, is spaced apart from the primary inflatable element a distance sufficient to accommodate the lower oesophageal sphincter therebetween. Preferably, the secondary inflatable element is proximally spaced apart from the primary inflatable element a distance in the range of 10 mm to 30 mm.

In another embodiment of the invention a third communicating means is provided for communicating the secondary hollow interior region of the secondary inflatable element for accommodating an inflating medium into the secondary hollow interior region for inflating the secondary inflatable element. Advantageously, the third communicating means is independent of the first communicating means for facilitating inflating of the secondary inflatable element independently of the primary inflatable element.

In one embodiment of the invention the secondary inflatable element comprises an elastic material, and in an alternative embodiment of the invention the secondary inflatable element comprises a non-elastic material.

In another embodiment of the invention at least one secondary stimulating electrode is located within the secondary hollow interior region on one of the catheter and an inner surface of the secondary inflatable element for receiving a stimulating signal, and at least one secondary sensing electrode is located in the secondary hollow interior region on one of the catheter and the inner surface of the secondary inflatable element axially spaced apart from the at least one secondary stimulating electrode for producing a secondary signal indicative of one of the transverse cross-sectional area and the diameter of the secondary inflatable element in response to a secondary stimulating signal applied to the at least one secondary stimulating electrode when the secondary hollow interior region is inflated with an electrically conductive medium.

Preferably, a pair of spaced apart secondary stimulating electrodes are provided, and the at least one secondary sensing electrode is located between the secondary stimulating electrodes and spaced apart therefrom.

In another embodiment of the invention a plurality of spaced apart secondary sensing electrodes are provided, the secondary sensing electrodes being located between the secondary stimulating electrodes and spaced apart therefrom.

In another embodiment of the invention a fourth communicating means is provided for communicating with the secondary stimulating and sensing electrodes.

In one embodiment of the invention the catheter extends through the secondary inflatable element and defines with the secondary inflatable element the secondary hollow interior region of annular shape when the secondary inflatable element is inflated.

In one embodiment of the invention an inflating means is provided for inflating the primary and secondary inflatable elements. Preferably, the inflating means is adapted for inflating the primary and secondary inflatable elements independently of each other. Advantageously, the inflating means comprises a primary inflating means adapted for inflating the primary inflatable element and a secondary inflating means adapted for inflating the secondary inflatable element.

Advantageously, the primary and secondary inflatable elements are inflatable with an electrically conductive inflating medium, and ideally, are independently inflatable by the primary inflating means.

In one embodiment of the invention the inflating medium comprises a saline solution.

Alternatively, the secondary inflatable element is inflatable with an electrically non-conductive inflating medium, for example, air.

In another embodiment of the invention a signal generating means is provided, the signal generating means being adapted for applying a primary stimulating signal to the at least one primary stimulating electrode, and preferably, the primary stimulating signal is a primary stimulating current signal.

In another embodiment of the invention the signal generating means is adapted for applying a secondary stimulating signal to the at least one secondary stimulating electrode, and preferably, the secondary stimulating signal is a secondary stimulating current signal.

In another embodiment of the invention a signal processing means is provided for processing the primary signal produced on the at least one primary sensing electrode, and preferably, the primary signal produced on the primary sensing electrode is a voltage signal.

Ideally, the signal processing means is adapted for determining one of the transverse cross-sectional area and the diameter of the primary inflatable element adjacent each primary sensing electrode from the corresponding primary signal produced thereon.

In a further embodiment of the invention the signal processing means is adapted for determining one of the transverse cross-sectional area and the diameter of the secondary inflatable element adjacent each secondary sensing electrode from the corresponding secondary signal produced thereon.

Advantageously, a display means is provided for displaying data indicative of the one of the transverse cross-sectional area and the diameter of the primary inflatable element adjacent the respective ones of the primary sensing electrodes.

Advantageously, the display means is adapted for displaying data indicative of one of the transverse cross-sectional area and the diameter of the secondary inflatable element adjacent each secondary sensing electrode.

In one embodiment of the invention the data indicative of the one of the transverse cross-sectional area and the diameter of the primary element is displayed numerically. Preferably, a graphical representation of the primary inflatable element is displayed graphically on the display means.

In a further embodiment of the invention the display means is adapted for displaying the pressure of the inflating medium in the primary hollow interior region of the primary inflatable element.

In a still further embodiment of the invention, an imaging means is located for producing signals indicative of a captured image of the interior of the gastric sleeve. Preferably, the imaging means is located in the catheter.

In one embodiment of the invention the imaging means is located within the primary inflatable element.

In another embodiment of the invention the imaging means is located intermediate the primary inflatable element and the secondary inflatable element.

In another embodiment of the invention the imaging means is located adjacent the distal end of the catheter.

Preferably, the imaging means is recessed into the catheter.

Advantageously, the imaging means comprises a CMOS imaging chip.

In one embodiment of the invention, a fifth communicating means is provided for communicating with the imaging means.

Preferably, the display means is adapted for displaying an image of the interior of the gastric sleeve captured by the imaging means from the signals produced by the imaging means.

In one embodiment of the invention the data processing means is adapted for processing the signals received from the imaging means prior to the captured image of the interior of the gastric sleeve being displayed on the display means.

In a further embodiment of the invention the primary inflatable element is of a transparent material.

In another embodiment of the invention the device further comprises a former adapted for locating in the stomach of a subject for facilitating formation of an oversized gastric sleeve therearound.

Preferably, the former is a hollow former adapted to accommodate the primary inflatable element therein.

The invention also provides a method for monitoring the transverse cross-section of a gastric sleeve during formation thereof in a subject in a sleeve gastrectomy, the method comprising locating a primary inflatable element in the stomach of the subject, inflating the primary inflatable element with an inflating medium to a transverse cross-section approximating to the internal transverse cross-section to which the gastric sleeve is to be formed, suturing or stapling the stomach to form the gastric sleeve around the primary inflatable element, and monitoring one of the transverse cross-sectional area of the primary inflatable element, the diameter of the primary inflatable element and the pressure of the inflating medium in the primary inflatable element during suturing or stapling of the stomach in order to produce the gastric sleeve of the desired transverse cross-section.

In one embodiment of the invention the pressure of the inflating medium in the primary inflatable element is monitored during suturing or stapling of the stomach in order to determine if the stomach is being excessively stretched around the primary inflatable element during suturing or stapling of the stomach.

Preferably, the portion of the stomach which is to form the gastric sleeve is urged around the inflated inflatable element prior to suturing or stapling, and the pressure of the inflating medium in the primary inflatable element is monitored as the portion of the stomach is being urged around the primary inflatable element.

In one embodiment of the invention the primary inflatable element is an elongated primary inflatable element and is located in the stomach to extend from a location adjacent the lower oesophageal sphincter.

Preferably, the primary inflatable element extends into the antrum.

Advantageously, the primary inflatable element extends to a location adjacent the pylorus.

Advantageously, the primary inflatable element is located towards a distal end of a catheter, and the primary inflatable element on the catheter is entered orally into the stomach of the subject through the oesophagus.

In another embodiment of the invention a secondary inflatable element is located on the catheter spaced apart from one of a proximal end and a distal end of the primary inflatable element, and the catheter is urged through the stomach of the subject until the secondary inflatable element is located in one of the duodenum and the oesophagus adjacent the corresponding one of the pylorus and the lower oesophageal sphincter. Preferably, the secondary inflatable element is located spaced apart from the distal end of the catheter, and the catheter is manoeuvred until the secondary inflatable element is located in the duodenum adjacent the pylorus.

In another embodiment of the invention, the primary inflatable element is located in the stomach with the pylorus located between the primary and secondary inflatable elements.

Preferably, the pylorus is engaged by the primary and secondary inflatable elements.

Advantageously, the secondary inflatable element is inflated for locating the primary inflatable element in the stomach.

In a further embodiment of the invention, the primary and secondary inflatable elements are provided by the device according to the invention, and the primary stimulating signal is applied to the primary stimulating electrodes, and the primary signals produced on the primary sensing electrodes indicative of the one of the transverse cross-sectional area and the diameter of the primary inflatable element are read, and the one of the transverse cross-sectional area and the diameter of the primary inflatable element adjacent each primary sensing electrode is computed.

In one embodiment of the invention the primary inflatable element is inflated with a saline solution.

In another embodiment of the invention the secondary inflatable element is inflated with a saline solution.

In another embodiment of the invention a former is placed in the stomach prior to forming the gastric sleeve around the primary inflatable element, and the gastric sleeve is formed around the former to a transverse cross-sectional area greater than the desired transverse cross-sectional area, and the stomach is sutured or stapled along a preliminary stapling line.

Preferably, on completion of suturing or stapling the stomach along the preliminary stapling line, the former is removed and the primary inflatable element is inflated to the internal transverse cross-sectional area to which the gastric sleeve is to be formed, and the gastric sleeve is formed around the primary inflatable element.

In one embodiment of the invention the former is an elongated hollow former. Preferably, the primary inflatable element is located in the former. Advantageously, the primary inflatable element is inserted into the stomach in the former.

The advantages of the invention are many. A particularly important advantage of the invention is that it permits monitoring of the interior of the gastric sleeve as the gastric sleeve is being formed by either suturing or stapling the stomach along the suturing or stapling line. This permits the transverse cross-sectional area of the gastric sleeve to be monitored during its formation, and if during formation of the gastric sleeve a part of the stomach is being sutured or stapled at a location which would form a reduction in the transverse cross-sectional area of the gastric sleeve, which in turn would result in necking of the gastric sleeve, corrective action can be taken in order to avoid such necking of the gastric sleeve.

Additionally, by monitoring the pressure of the inflating medium in the primary inflatable element during formation of the gastric sleeve, if the gastric sleeve is being excessively stretched around the primary inflatable element, this will result in an increase in pressure in the inflating medium within the primary inflatable element, and a suitable signal can be presented to the surgeon or physician indicating the increase in the pressure of the inflating medium, and the stretching of the stomach around the primary inflatable element can be reduced to a more appropriate level.

By presenting data indicative of the pressure of the inflatable medium in the primary inflatable element and data indicative of the transverse cross-sectional area or the diameter of the primary inflatable element adjacent the primary sensing electrodes, the surgeon or physician can readily monitor the transverse cross-sectional area or the diameter of the interior of the gastric sleeve during formation thereof, and the surgeon or physician can also determine if the stomach is being excessively stretched around the primary inflatable element.

The provision of an imaging means provides a further advantage in that the surgeon or physician can be presented with images of the interior of the gastric sleeve which thus allows monitoring of the suturing or stapling for bleeding and other defects. By locating the imaging means within the primary inflatable element and by providing the primary inflatable element of a transparent material, imaging of the interior of the gastric sleeve can be carried out during suturing or stapling of the stomach to form the gastric sleeve, and thus, the surgeon or physician can be presented with images of the interior of the gastric sleeve during its formation.

Figure 5:
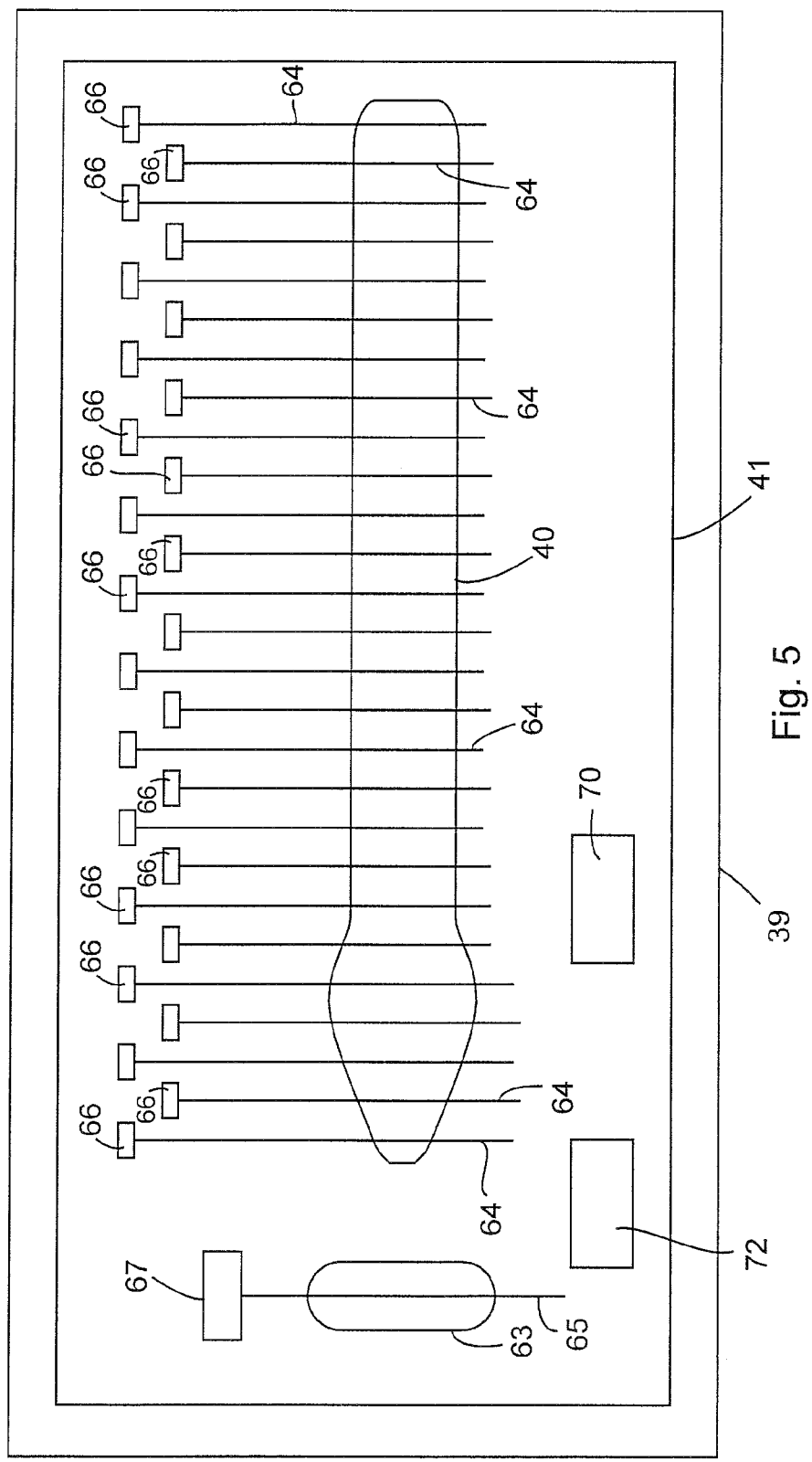
Figure 6:
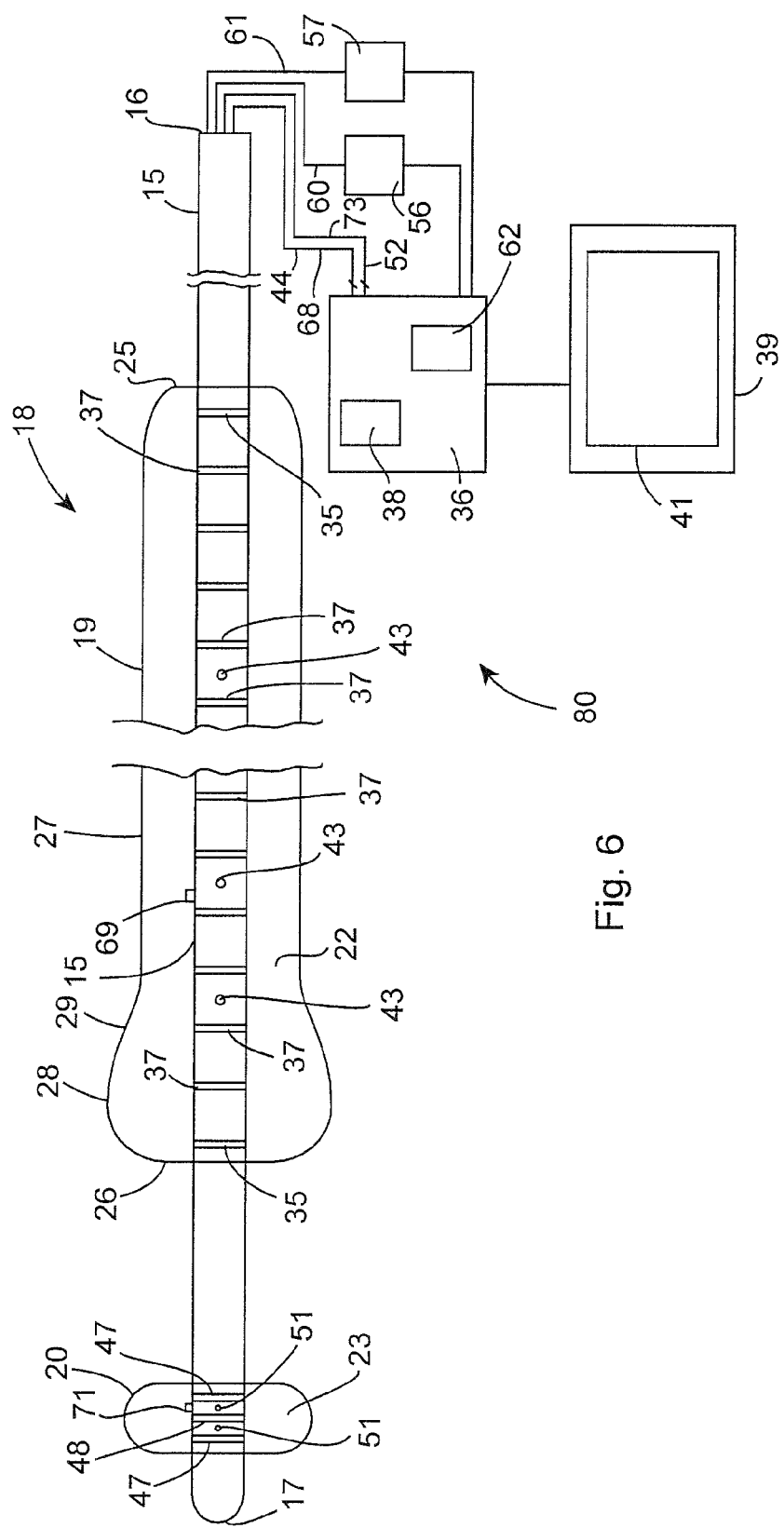
Figure 10:
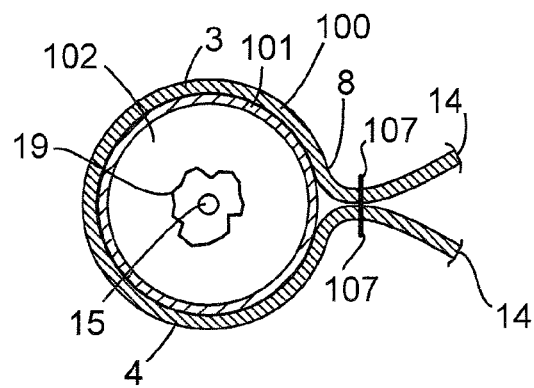
Figure 9:
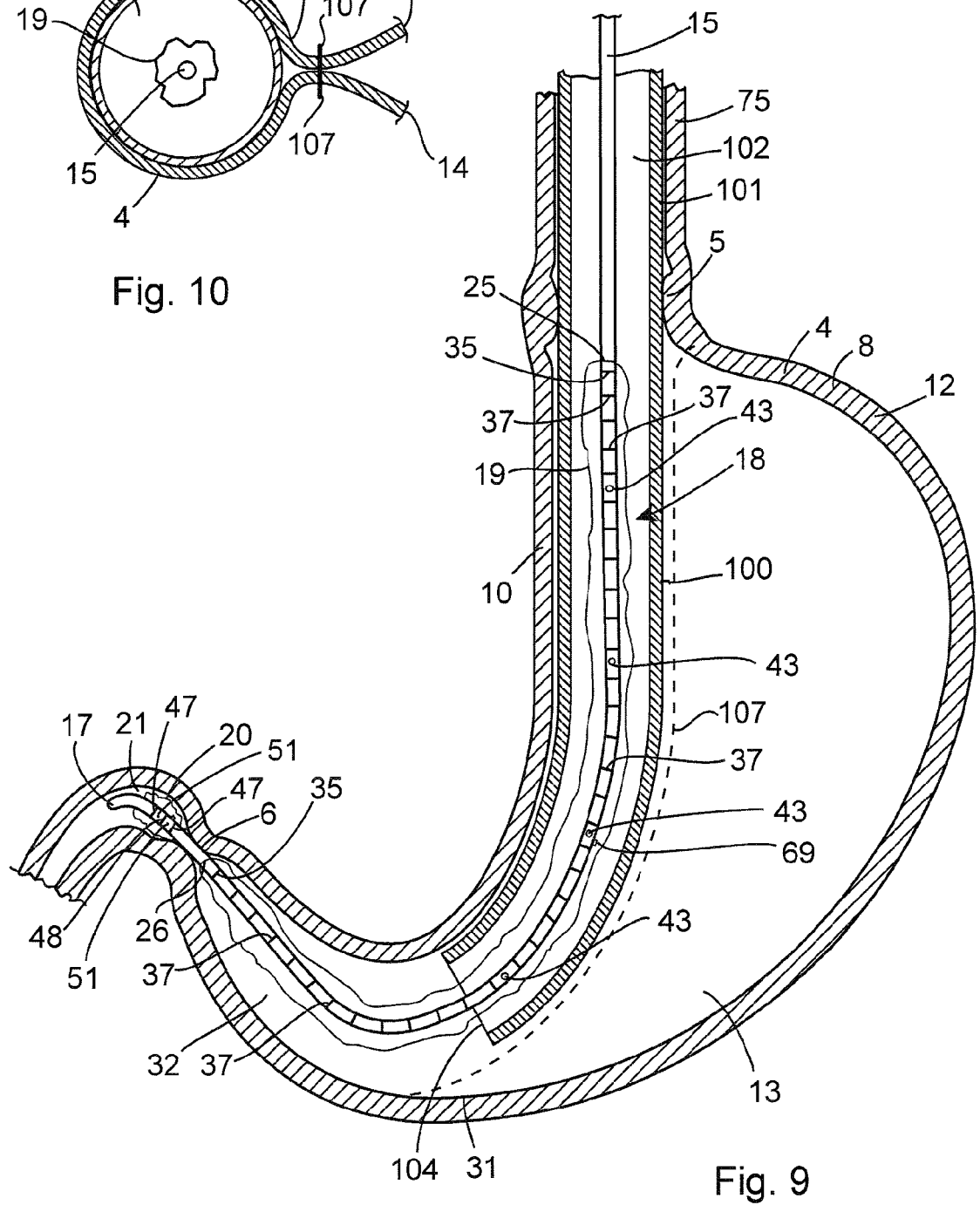

The invention will be more clearly understood from the following description of some preferred embodiments thereof, which are given by way of example only, with reference to the accompanying drawings, in which:

FIG. 1 is a partly transverse cross-sectional side elevational view and a partly block representational view of a device according to the invention for facilitating monitoring of the transverse cross-sectional area of a gastric sleeve during formation thereof in a stomach, FIG. 2 is a transverse cross-sectional area of a portion of the device of FIG. 1 on the line II-II of FIG. 1, FIG. 3 is a cross-sectional side elevational view of the device of FIG. 1 in use in the formation of a gastric sleeve, FIG. 4 is a transverse cross-sectional end elevational view of the device of FIG. 1 also in use in the formation of a gastric sleeve, FIG. 5 is a front elevational view of a portion of the device of FIG. 1, FIG. 6 is a view similar to FIG. 1 of a device according to another embodiment of the invention for facilitating monitoring of the transverse cross-sectional area of a gastric sleeve during formation thereof in the stomach, FIG. 7 is a view similar to FIG. 1 of a device according to another embodiment to of the invention for facilitating monitoring of the transverse cross-sectional area of a gastric sleeve during formation thereof in the stomach, and FIG. 8 is a cross-sectional elevational view of a detail of the device of FIG. 7, FIG. 9 is a view similar to FIG. 3 illustrating the formation of a gastric sleeve by a method according to another embodiment of the invention, and FIG. 10 is a view similar to FIG. 4 illustrating the formation of a gastric sleeve by the method of FIG. 9.

Referring to the drawings, and initially to FIGS. 1 to 5, there is illustrated a device according to the invention, indicated generally by the reference numeral 1, for monitoring the transverse cross-section of a gastric sleeve 3 as the gastric sleeve 3 is being formed in a stomach 4, see FIGS. 3 and 4. The gastric sleeve 3 is formed to extend from the lower oesophageal sphincter 5 to the pylorus 6. Before describing the device 1 in detail, the procedure for forming the gastric sleeve 3 will first be briefly described.

The procedure which is commonly referred to as a sleeve gastrectomy procedure is carried out by suturing or stapling, and generally stapling opposite portions 7 of the wall 8 of the stomach 4 together along a line 9 which for convenience is referred to hereinafter as a stapling line 9 and which extends from adjacent the lower oesophageal sphincter 5 to the pylorus 6, see FIGS. 3 and 4. The stapling line 9 is located closer to a side 10 of lesser curvature of the stomach 4 which is to form a part of the gastric sleeve 3, than to an opposite side 12, namely, the side 12 of greater curvature of the stomach 4 which after suturing or stapling of the opposite portions 7 of the wall 8 of the stomach 4 is severed from the gastric sleeve 3. The stapling line 9 is spaced apart from the side 10 of lesser curvature of the stomach 4 an appropriate distance to produce the gastric sleeve 3 of the desired diameter. After completion of suturing or stapling of the opposite portions 7 of the wall 8 of the stomach 4 along the stapling line 9 to produce the gastric sleeve 3 extending from the lower oesophageal sphincter 5 to the pylorus 6, the remaining part 13 of the stomach 4 is severed at 14 from the gastric sleeve 3 and is removed.

Turning now to the device 1 and referring in particular to FIGS. 1 to 5, the device 1 is provided in the form of a balloon catheter 18 and comprises an elongated catheter 15 extending from a proximal end 16 to a distal end 17. A primary inflatable element, namely, a primary balloon 19 is located on the catheter 15 towards the distal end 17 thereof around which the portion of the stomach 4 which is to form the gastric sleeve 3 is stretched and wrapped during formation of the gastric sleeve 3, so that the transverse cross-sectional area of the gastric sleeve 3 can be monitored during formation thereof, as will be described below. A secondary inflatable element provided by a secondary balloon 20 is located on the catheter 15 adjacent the distal end 17 thereof and spaced apart from the primary balloon 19 for engaging the duodenum 21 adjacent the pylorus 6, for in turn locating and anchoring the device 1 in the subject with the primary balloon 19 extending through the stomach 4 from the lower oesophageal sphincter 5 to the pylorus 6, in order that the gastric sleeve 3 may be formed around the primary balloon 19. The catheter 15 extends coaxially through the primary balloon 19 and the secondary balloon 20 so that when the primary and secondary balloons 19 and 20 are inflated, the catheter 15 defines with the primary balloon 19 a primary hollow interior region 22 and with the secondary balloon 20 a secondary hollow interior region 23.

The primary balloon 19 is of a non-elastic pliable transparent material and extends from a proximal end 25 to a distal end 26. The primary balloon 19 is shaped so that when inflated the primary balloon 19 defines an elongated main cylindrical portion 27 of constant transverse cross-section extending from the proximal end 25 thereof towards the distal end 26. The transverse cross-sectional area of the main portion 27 of the primary balloon 19 when inflated is similar to the desired transverse cross-section to which the gastric sleeve 3 is to be formed. The main portion 27 of the primary balloon 19 terminates in a distal portion 28 which is of circular transverse cross-section and of diameter greater than the diameter of the main portion 27. An intermediate portion 29 of the primary inflatable element 19 located between the distal portion 28 and the main portion 27 tapers proximally from the distal portion 28 to the main portion 27. A distal tapering portion 30 of the primary inflatable element tapers from the distal portion 28 to the catheter 15. The distal tapering portion 30 is shaped for locating in the antrum 32 adjacent the pylorus 6, and the distal portion 28 and the intermediate portion 29 are adapted for locating in a portion 31 of the stomach adjacent the antrum 32, so that the gastric sleeve 3 is formed to diverge at its distal end to the antrum 32.

The advantage of providing the primary balloon 15 with the intermediate portion 29, which tapers proximally to the cylindrical portion 27, is that the gastric sleeve 3 when formed around the primary balloon 19 comprises an elongated portion of constant transverse cross-section extending from the lower oesophageal sphincter 5 which is formed around the main cylindrical portion 27 of the primary balloon 19, and a distal portion which is formed around the intermediate portion 29 of the primary balloon 19, and which diverges slightly outwardly from the constant cross-section portion of the gastric sleeve 3 towards the antrum 32. This, thus, avoids any danger of the pylorus being inadvertently stapled or sutured during stapling or suturing of the stomach 4 along the stapling line 9.

The secondary balloon 20 is of an elastic material and is configured to be of circular transverse cross-section when inflated. The spacing between the secondary balloon 20 and the primary balloon 19 adjacent the distal end 26 of the primary balloon 19 is approximately 15 mm in order to accommodate the pylorus 6 between the primary and secondary balloons 19 and 20, with the pylorus 6 snugly engaged between the primary and secondary balloons 19 and 20.

A pair of spaced apart primary stimulating electrodes 35 are located on the catheter 15 within the primary hollow interior region 22 adjacent the respective opposite proximal and distal ends 25 and 26 thereof for receiving a primary stimulating signal, which in this embodiment of the invention is a primary stimulating current signal from a control circuit 36 as will be described below. A plurality of spaced apart primary sensing electrodes 37 are located within the primary hollow interior region 22 of the primary balloon 19 on the catheter 15, and between and spaced apart from the primary stimulating electrodes 35 for producing primary voltage signals indicative of the transverse cross-sectional area and the diameter of the primary balloon 19 adjacent the respective primary sensing electrodes 37 in response to the primary stimulating current signal applied to the primary stimulating electrodes 35 when the primary balloon 19 is inflated with an electrically conductive inflating medium. In this case the inflating medium is a saline solution. The primary stimulating and sensing electrodes 35 and 37 are electrically conductive band electrodes and extend around the catheter 15.

A data processing circuit 38 located in the control circuit 36 processes the primary voltage signals produced on the primary sensing electrodes 37 for determining either the transverse cross-sectional area or the diameter of the primary balloon 19 adjacent the respective primary sensing electrodes 37. The control circuit 36 operates a display means, namely, a visual display unit 39 for displaying a graphical representation 40 of the transverse cross-section of the primary balloon 19 on a visual display screen 41 of the visual display unit 39, and also for displaying values of the transverse cross-sectional area or the diameter of the primary balloon 19 on the visual display screen 41 adjacent the primary sensing electrodes 37 as will be described below.

A first communicating means, namely, a first lumen 42 extending from the proximal end 16 of the catheter 15 to the primary balloon 19 accommodates the saline inflating medium to the primary balloon 19 for inflating thereof. A plurality of primary ports 43 extending radially into the catheter 15 communicate with the first lumen 42 for accommodating the saline inflating medium into the primary hollow interior region 22 of the primary balloon 19 for inflating thereof. A second communicating means comprising a plurality of mutually insulated electrically conductive primary wires 44 communicate the primary stimulating and sensing electrodes 35 and 37 with the control circuit 36 for applying the primary stimulating current signal to the primary stimulating electrodes 35 and for conducting the primary voltage signals produced on the primary sensing electrodes 37 to the data processing circuit 38. A second lumen 45 extending from the proximal end 16 of the catheter 15 to the primary balloon 19 accommodates the primary wires 44 through the catheter 15, and radial bores 46 or an axially extending slot extending from the second lumen 45 through the catheter 15 accommodate the primary wires 44 from the second lumen 45 to the corresponding primary stimulating and sensing electrodes 35 and 37.

A pair of spaced apart secondary stimulating electrodes 47 are mounted on the catheter 15 within the secondary hollow interior region 23 of the secondary balloon 20 for receiving a secondary stimulating signal, in this embodiment of the invention a secondary stimulating current signal from the control circuit 36. A single secondary sensing electrode 48 is located on the catheter 15 between and spaced apart from the secondary stimulating electrodes 47 within the secondary hollow interior region 23 for producing a secondary voltage signal indicative of the transverse cross-sectional area or the diameter of the secondary balloon 20 adjacent the secondary sensing electrode 48 in response to the secondary stimulating current signal on the secondary stimulating electrodes 47 when the secondary balloon 20 is inflated with the saline inflating medium.

A third communicating means, namely, a third lumen 50 extending from the proximal end 16 of the catheter 15 to the secondary balloon 20 accommodates the saline inflating medium to the secondary balloon 20 for inflating thereof. A pair of secondary ports 51 extending radially through the catheter 15 from the third lumen 50 communicates the third lumen 50 with the secondary hollow interior region 23 of the secondary balloon 20 for accommodating the saline inflating medium into the secondary hollow interior region 23 of the secondary balloon 20 for inflating thereof. A fourth communicating means, namely, three mutually insulated electrically conductive secondary wires 52 communicate the secondary stimulating and sensing electrodes 47 and 48 with the control circuit 36 for applying the secondary stimulating current signal to the secondary stimulating electrodes 47 and for reading the secondary voltage signal produced on the secondary sensing electrode 48 in response to the secondary stimulating current signal applied to the secondary stimulating electrodes 47 when the secondary balloon 20 is inflated with the saline inflating medium. A fourth lumen 53 extending through the catheter 15 from the proximal end 16 to the secondary balloon 20 accommodates the secondary wires 52, and radial bores 54 or an axially extending slot extending radially through the catheter 15 from the fourth lumen 53 accommodate the secondary wires 52 to the secondary stimulating and sensing electrodes 47 and 48.

An inflating means, which may be provided as a single inflating means or as two inflating means, namely, a primary inflating means and a secondary inflating means, in this embodiment of the invention comprises a primary inflating pump 56 for inflating the primary balloon 19 and a secondary inflating pump 57 for inflating the secondary balloon 20. Both the primary inflating pump 56 and the secondary inflating pump 57 are illustrated in block representation in FIG. 1, and are coupled to the first lumen 42 and the third lumen 50 by primary and secondary pipe lines 60 and 61, respectively. The primary and secondary inflating pumps 56 and 57 are operated under the control of the control circuit 36 to pump the saline inflating medium through the first and third lumens 42 and 50 to the primary and secondary balloons 19 and 20, respectively, for inflating the primary and secondary balloons 19 and 20 independently of each other. Where a single inflating means, such as a single pump or a single syringe is provided a valving system is provided so that the primary and secondary balloons 19 and 20 are inflated independently of each other. The primary and secondary inflating pumps 56 and 57 are operated under the control of the control circuit 36 for deflating the primary and secondary balloons 19 and 20, respectively.

In this embodiment of the invention a signal generator 62 located within the control circuit 36 and operated under the control of the control circuit 36 generates and selectively applies the primary and secondary stimulating current signals to the primary and secondary stimulating electrodes 35 and 4, respectively. The data processing circuit 38 as well as reading the primary voltage signals from the primary sensing electrodes 37 also reads the secondary voltage signal from the secondary sensing electrode 48, and computes either or both the transverse cross-sectional area and the diameter of the primary balloon 19 and the secondary balloon 20 adjacent the primary and secondary sensing electrodes 37 and 48, respectively. The control circuit 36 operates the visual display unit 39 for displaying both the graphical representation 40 of the primary balloon 19 and a graphical representation 63 of the cross-section of the secondary balloon 20 on the visual display screen 41.

Graphical representations of the primary and secondary sensing electrodes 37 and 48 in the form of lines 64 and 65, respectively, are displayed on the visual display screen 41 under the control of the control circuit 36. The graphical representations 64 and 65 of the primary and secondary sensing electrodes 37 and 48 are displayed on the visual display screen 41 at positions along the graphical representations 40 and 63, respectively, at positions which correspond to the positions of the primary and secondary sensing elements 37 and 48 along the primary and secondary balloons 19 and 20. Numerical values of the transverse cross-sectional area or the diameter of the primary balloon 19 and the secondary balloon 20 adjacent the corresponding primary and secondary sensing electrodes 37 and 48, respectively, are displayed in windows 66 and 67, respectively, on the visual display screen 41 of the visual display unit 39 adjacent the corresponding graphical representations 64 and 65, respectively, of the primary and secondary sensing electrodes 37 and 48.

The computation of the transverse cross-sectional areas and/or diameters of the primary and secondary balloons 19 and 20 adjacent the primary and secondary sensing electrodes 37 and 48 from the voltage signals read from the primary and secondary sensing electrodes 37 and 48 will be well known to those skilled in the art, and is described in PCT Publication Application Specification No. WO 2009/001328.

A primary pressure sensing means, namely, a primary pressure transducer 69 is located on the catheter 15 within the primary hollow interior region 22 of the primary balloon 19 for monitoring the pressure of the saline inflating medium within the primary balloon 19. A plurality of mutually insulated electrically conductive wires 68 from the primary pressure transducer 69 are accommodated through the second lumen 45 to the control circuit 36. The data processing circuit 38 reads signals from the primary pressure transducer 69 to determine the pressure of the saline inflating medium in the primary balloon 19. A graphical and/or numerical display of the computed pressure in the primary balloon 19 is displayed on the visual display unit 39 under the control of the control circuit 36 for facilitating monitoring of the pressure in the primary balloon 19 during suturing or stapling of the stomach 4 to form the gastric sleeve 3. In this embodiment of the invention the numerical value of the pressure of the saline inflating medium in the primary balloon 19 is displayed in a window 70 in the visual display screen 41.

A secondary pressure sensing means comprising a secondary pressure transducer 71 is located on the catheter 15 in the secondary balloon 20 for monitoring the pressure of the saline inflating medium in the secondary balloon 20. Mutually insulating electrically conductive wires 73 from the pressure transducer 71 extend through the fourth lumen 53 to the data processing circuit 38 where signals from the secondary pressure transducer 71 are read and converted to pressure values, which in turn are displayed in a window 72 in the visual display screen 41. This permits a physician or surgeon to monitor the pressure of the saline inflating medium in the secondary balloon 20.

The use of the device 1 in facilitating monitoring the transverse cross-section of the gastric sleeve 3 during formation thereof in a sleeve gastrectomy will now be described with reference to FIGS. 3 to 5. Prior to commencing the sleeve gastrectomy procedure, the device 1 with the primary and secondary balloons 19 and 20 deflated, is inserted orally through the oesophagus 75 and into the stomach 4 through the lower oesophageal sphincter 5 and through the stomach 4 to the antrum 32. The distal end 17 of the catheter 15 is urged through the pylorus 6 until the secondary balloon 20 is located in the duodenum 21. Location of the secondary balloon 20 in the duodenum 21 is typically determined by laparoscopic visualisation. Once the secondary balloon 20 is located in the duodenum 21, the control circuit 36 is activated to operate the secondary pump 57 to initially inflate the secondary balloon 20. The signal generator 62 is operated under the control of the control circuit 36 for applying the secondary stimulating current signal to the secondary stimulating electrodes 47. The data processing circuit 38 under the control of the control circuit 36 computes the transverse cross-sectional area or the diameter of the secondary balloon 20 from the secondary voltage signal read from the secondary sensing electrode 48. The graphical representation 63 of the secondary balloon 20 is displayed on the visual display screen 41, and the computed transverse cross-sectional area or the diameter of the secondary balloon 20 adjacent the secondary sensing electrode 48 is displayed in the window 67 on the visual display screen 41, see FIG. 5. Signals read by the data processing circuit 38 from the secondary pressure transducer 71 are converted to pressure values, and the pressure of the inflating medium in the secondary balloon 20 is displayed in the window 72 of the visual display screen 41. A surgeon or physician can then determine from the data displayed on the visual display screen 41 when to terminate inflating of the secondary balloon 20 so that the cross-section of the secondary balloon 20 is of similar cross-section to the internal cross-section of the duodenum 21.

Alternatively, the control circuit 36 may also be programmed to monitor the transverse cross-sectional area or the diameter of the secondary balloon 20, or the pressure of the inflating medium in the secondary balloon 20, and when the secondary balloon 20 has been inflated to a predefined transverse cross-sectional area or diameter, or to a predefined pressure, the control circuit 36 would merely deactivate the secondary pump 57. In a further alternative method the secondary balloon 20 may be inflated by a predefined volume of the inflating medium in order to inflate the secondary balloon 20 to a predefined diameter. In which case, it would not be necessary to monitor the transverse cross-sectional area, diameter or pressure of the secondary balloon 20 during inflating thereof. The surgeon or physician may also monitor the pressure of the saline inflating medium in the secondary balloon 20 in the window 72 in the visual display screen 41 to ensure that the pressure in the secondary balloon 20 is not excessive.

On the secondary balloon 20 being appropriately inflated, the device 1 is withdrawn slightly in order to urge the inflated secondary balloon 20 into engagement with the pylorus 6 in order to correctly locate the primary balloon 19 in the stomach 4 of the subject. With the secondary balloon 20 abutting the pylorus 6, the primary balloon 19 is correctly located in the stomach 4 to enable the gastric sleeve 3 to be formed around the primary balloon 19.

The primary balloon 19 is then inflated by the primary pump 56 under the control of the control circuit 36. During inflating thereof, the primary stimulating current signal from the signal generator 62 is applied under the control of the control circuit 36 to the primary stimulating electrodes 35, and the data processing circuit 38 reads the primary voltage signals produced on the primary sensing electrodes 37 and computes the transverse cross-sectional area or diameter of the primary balloon 19 adjacent the respective primary sensing electrodes 37. The computed transverse cross-sectional areas or diameters are displayed in windows 66 on the visual display screen 41 together with the graphical representation 40 of the primary balloon 19. The values of the transverse cross-sectional areas or diameters in the windows 66 as well as the graphical representation 40 of the primary balloon 19 on the visual display screen 41 are continuously updated as the inflating procedure continues.

The control circuit 36 is programmed to deactivate the primary pump 56 in order to terminate inflating of the primary balloon 19 when a predefined volume of the saline inflating medium has been delivered into the primary balloon 19, or when the transverse cross-sectional area or diameter of the main portion 27 of the primary balloon 19 has reached the desired value, which is programmed by the surgeon or physician into the control circuit 36. The desired value of the transverse cross-sectional area or the diameter of the main portion 27 of the primary balloon 19 is selected to approximate with the desired transverse cross-sectional area or diameter to which the gastric sleeve 3 is to be formed. The pressure of the saline inflating medium within the primary hollow interior region 22 of the primary balloon 19 is continuously monitored by the control circuit 27, and the numerical value of the pressure is displayed in the window 70 on the visual display screen 41 and continuously updated.

Once the primary balloon 19 has been inflated with the predefined volume of saline inflating medium to the desired transverse cross-sectional area or diameter, or has been inflated to the desired transverse cross-sectional area or diameter by monitoring the primary voltage signals produced on the primary sensing electrodes 37, and the main portion 27 of the primary balloon 9 is of the desired transverse cross-sectional area or diameter, or the primary balloon has been inflated to a predefined pressure, the surgeon or physician urges the portion of the stomach to form the gastric sleeve 3 around the inflated primary balloon 19 and determines where the line 9 of suturing or stapling is to be formed along the stomach. Suturing or stapling is commenced and the surgeon or physician monitors the graphical representation 40 of the primary balloon 19 on the visual display screen 41 as well as the values of the transverse cross-sectional area or the diameter values in the windows 66 of the visual display screen 41, and also monitors the pressure in the window 70 in the visual display screen 41, which is the value of the pressure which is being induced in the saline inflating medium in the primary balloon 19 by the gastric sleeve 3 as the gastric sleeve 3 is being progressively formed by suturing or stapling the stomach along the line 9. The pressure of the saline inflating medium in the primary balloon 19 is monitored to ensure that the portion of the stomach 4 forming the gastric sleeve 3 is not being excessively stretched around the primary balloon 19. Any excessive stretching or tightening of the stomach around the primary balloon 19 to form the gastric sleeve 3 would result in the gastric sleeve 3 shrinking to a lesser diameter than the desired diameter when the primary balloon 19 is deflated.

Additionally, the graphical representation 40 of the primary balloon 19 as well as the values of the transverse cross-sectional area or the diameter of the primary balloon 19 in the windows 66 are monitored in order to ensure that the suturing or stapling of the stomach 4 is being carried out along the desired stapling line 9 and is not arcing inwardly, which would otherwise result in necking of the gastric sleeve 3 intermediate the ends thereof. If arcing of the stapling line 9 is detected corrective action is taken.

Alternatively, or additionally, the control circuit 36 may be programmed to produce a visual and/or audible alarm in response to the pressure of the saline inflating medium in the primary balloon 19 increasing above a predefined value during suturing or stapling of the stomach 4. The control circuit 36 may also be programmed to produce a visual and/or audible alarm in response to the suturing or stapling of the stomach 4 diverging from the desired stapling line 9, which would result in necking of the gastric sleeve 3 intermediate the ends thereof.

On completion of the suturing or stapling, the remaining part 13 of the stomach 4 is severed from the gastric sleeve 3 at 14 and removed. The primary and secondary balloons 19 and 20 are deflated and the device 1 is removed from the subject.

The gastric sleeve 3 may be formed to any desired diameter, however, typically, the gastric sleeve 3 is formed to a diameter in a range of approximately 11 mm to 20 mm, although the diameter of the gastric sleeve may be greater than 20 mm or less than 11 mm. Where the primary balloon 19 is of a non-expandable material, a range of balloon catheters 18 will be provided with respective primary balloons which when inflated inflate to respective different diameters. For example, one of the balloon catheters would be provided with a primary balloon of an inflated diameter of 11 mm, while another would be provided with a primary balloon with an inflated diameter of 12 mm, and a further balloon catheter would be provided with a primary balloon with an inflated diameter of 13 mm, and so on in millimetre steps up to 20 mm. A balloon catheter with a primary balloon of the appropriate inflated diameter would be selected to carry out the sleeve gastrectomy. Alternatively, the balloon catheter may be provided with a primary balloon of an expandable pliable material which could be inflated to any desired diameter within a predefined range, which could be, for example, from 11 mm to 20 mm.

In some cases, if when inflated the primary balloon 19 becomes relatively rigid, during formation of the gastric sleeve 3, the gastric sleeve, the antrum 32 and the pylorus 6 may be forced into straight alignment with each other. However, on deflating of the primary balloon 19, the gastric sleeve 3, the antrum 32 and the pylorus 6 take up their normal relaxed alignment illustrated in FIG. 3. However, if when inflated the primary balloon 19 does not become rigid, but remains relatively floppy, the gastric sleeve 3, the antrum 32 and the pylorus 6 typically remain in the relaxed configuration illustrated in FIG. 3 during formation of the gastric sleeve 3.

Referring now to FIG. 6, there is illustrated a device according to another embodiment of the invention, which is indicated generally by the reference numeral 80, for facilitating monitoring of the transverse cross-sectional area of a gastric sleeve as the gastric sleeve is being formed in the stomach of a subject during a sleeve gastrectomy procedure. The device 80 is substantially similar to the device 1 and similar components are identified by the same reference numerals. The main difference between the device 80 and the device 1 is in the shape of the distal portion of the primary balloon 19. In this embodiment of the invention, the primary balloon 19 terminates at the distal portion 28, and the distal tapering portion has been omitted. The primary balloon 19 in this embodiment of the invention is adapted to terminate in the portion 31 of the stomach adjacent the antrum 32, and the primary balloon 19 does not extend into the antrum 32. The spacing between the secondary balloon 20 and the primary balloon 19 is appropriately greater than the spacing between the primary and secondary balloons 19 and 20 of the device 1.

Otherwise, the device 80 is similar to the device 1, and its use is likewise similar to that of the device 1.

Referring now to FIGS. 7 and 8, there is illustrated a device according to another embodiment of the invention indicated generally by the reference numeral 90. The device 90 is substantially similar to the device 1 and similar components are identified by the same reference numerals. The only difference between the device 90 and the device 1 is that an imaging means, in this embodiment of the invention provided by a CMOS imaging chip 91 is located in a recess 92 in the catheter 15 in the primary hollow interior region 22 of the primary balloon 19 for capturing images of the interior of the gastric sleeve as the stomach is being sutured or stapled during formation of the gastric sleeve. In this embodiment of the invention the primary balloon 19 is also of a transparent material, and thus the interior of the gastric sleeve is visible to the CMOS imaging chip 91. A fifth communicating means, namely, mutually insulated electrically conductive wires 93 from the CMOS imaging chip 91 are passed through the second lumen 45 in the catheter 15 which accommodates the primary wires 44 from the primary stimulating and sensing electrodes 35 and 37, respectively, to the data processing circuit 38. Signals from the CMOS imaging chip are processed in the data processing circuit 38 and the processed signals from the data processing circuit 38 are relayed to the visual display unit 39 and images captured by the CMOS imaging chip 91 are displayed on the visual display screen 41 under the control of the control circuit 36. Thus, as the gastric sleeve is being formed by suturing or stapling the stomach along the stapling line 9, a surgeon can view the gastric sleeve as it is being formed, and check for bleeding or other suturing or stapling defects along the stapling line 9.

Otherwise, the device 90 and its use is similar to the device 1 and its use.

Referring now to FIGS. 9 and 10, a method according to another embodiment of the invention for monitoring the transverse cross-section of a gastric sleeve during formation thereof in a sleeve gastrectomy will now be described. In this embodiment of the invention prior to forming the gastric sleeve 3 around the primary balloon 19 of the balloon catheter 18, a slightly oversized gastric sleeve 100 is formed around an elongated hollow former 101 which defines an elongated through bore 102 extending therethrough from a proximal end (not shown) of the former 101 to a distal end 104 thereof. The former 101 is bendable along its axial length, but radially is substantially non-compressible, and may be of any suitable material, for example, a plastics material or the like. The former 101 is of slightly larger diameter than the diameter to which the gastric sleeve is to be ultimately formed, for example, if the gastric sleeve is ultimately to be formed to a diameter of 12 mm, the outer diameter of the former 101 would be approximately 15 mm, thus allowing the oversized gastric sleeve 100 to be formed to a diameter of approximately 15 mm.

The oversized gastric sleeve 100 is formed by stretching the portion of the stomach to form the gastric sleeve 100 around the former 101 in a similar manner to that described with respect to the formation of the gastric sleeve 3 around the primary balloon 19. As the stomach is being stretched around the former 101, the stomach is sutured or stapled along a preliminary stapling line 107 from the lower oesophageal sphincter 5 to the antrum 32. On completion of suturing or stapling the stomach 4 along the preliminary stapling line 107, the portion 13 of the stomach 4 is severed from the gastric sleeve 100 along the cut line 14. The former 101 is then removed from the formed oversized gastric sleeve 100, and the catheter 18 is positioned in the oversized gastric sleeve 100 as already described with reference to FIGS. 3 and 4 by inflating the secondary balloon 20 and positioning the catheter 15 with the secondary balloon 20 located in the duodenum 21 and abutting the pylorus 6.

The primary balloon 19 is then inflated as already described with reference to FIGS. 3 and 4. The gastric sleeve 3 is formed from the oversized gastric sleeve 100 to the desired cross-section by tightening the oversized gastric sleeve 100 around the primary balloon 19 and suturing or stapling the stomach 4 along the stapling line 9. The procedure for forming the gastric sleeve 3 around the primary balloon 9 is similar to that already described with reference to FIGS. 3 and 4.

In use, typically the former 101 with the balloon catheter 18 located in the through bore 102, and with the primary and secondary balloons 19 and 20 deflated is inserted orally into the stomach 4 through the oesophagus 75. The proximal end (not shown) of the former 101 remains extending from the mouth of the subject to facilitate subsequent removal of the former 101. The former 101 is located in the stomach 4 extending along the side 10 of the stomach 4 with the distal end 104 thereof located towards or close to the antrum 32. Once the former 101 has been correctly located in the stomach 4, the distal end 17 of the catheter with the primary and secondary balloons 19 and 20 deflated is urged through the pylorus 6 in order to locate the secondary balloon 20 in the duodenum 21 adjacent the pylorus 6. The primary and secondary balloons 19 and 20 of the balloon catheter 18 remain deflated while the oversized gastric sleeve 100 is being formed around the former 101.

On completion of the formation of the oversized gastric sleeve 100, the portion 13 of the stomach 4 is severed at 14 from the oversized gastric sleeve 100, and the former 101 is withdrawn from the stomach 4 through the oesophagus 75. The balloon catheter 18 is then accurately located in the now formed oversized gastric sleeve 100 as already described with reference to FIGS. 3 and 4 by initially inflating the secondary balloon 20 in the duodenum 21 and then manoeuvring the balloon catheter 18 until the secondary balloon 20 in the duodenum 21 snugly engages the pylorus 6. Thereafter the primary balloon 19 is inflated to the desired transverse cross-sectional area or diameter to which the gastric sleeve 3 is to be formed, and formation of the gastric sleeve 3 from the oversized gastric sleeve 100 is then carried out in a similar manner to that described with reference to FIGS. 3 and 4.

In this embodiment of the invention since the former 101 is bendable along its axial length, the former 101 when placed in the stomach 4 partly follows the curvature of the stomach adjacent the antrum 32, and accordingly, the portion of the stomach 4 which is to form the oversized gastric sleeve 100 can be stretched around the former 101 with minimal distortion of the alignment of the stomach 4 with the antrum 32 and the pylorus 6.

While the devices have been described as comprising balloon catheters with a secondary inflatable element for facilitating locating of the primary inflatable element in the stomach, while this is desirable, it is not essential. Indeed, it is envisaged that in certain cases the secondary inflatable element may be omitted. Alternatively, it is envisaged that the secondary inflatable element may be located proximally of the primary inflatable element, and would be spaced apart proximally from the primary inflatable element a distance sufficient to accommodate and to engage the lower oesophageal sphincter between the primary and secondary inflatable elements for locating and anchoring the primary balloon within the stomach.

It is envisaged that in certain cases, the secondary balloon may be provided without secondary stimulating and sensing electrodes, and in which case, it is envisaged that the secondary balloon could be inflated with the predefined volume of inflating medium or to a predefined pressure in order to inflate the secondary balloon to a desired diameter. Needless to say, where the secondary stimulating and sensing electrodes are omitted from the secondary balloon, the secondary balloon may be inflated with any inflating medium, either electrically conductive or non-conductive, for example, air.

While the primary balloon has been described as being of a non-elastic material, the primary balloon may be of any suitable material, either elastic or non-elastic. It will also be appreciated that the secondary balloon may be of an elastic or a non-elastic material.

While the material of the primary balloon has been described as being transparent, in the devices which are provided without an imaging means located within the primary inflatable element, the material of the primary inflatable element need not necessarily be transparent, it may be opaque or translucent. Indeed, it is envisaged that instead of locating the imaging means within the primary inflatable element, the imaging means may be located at the distal end of the catheter, or in the portion of the catheter intermediate the primary and secondary inflatable elements. In which case, imaging of the interior of the gastric sleeve would be carried out as the catheter is being withdrawn from the gastric sleeve.

While the imaging means has been described as comprising a CMOS imaging chip, any other suitable imaging means may be provided, and while it is desirable that the imaging means be recessed into the catheter, this is not essential.

While the inflating means for inflating the primary and secondary balloons have been described as being primary and secondary inflating pumps, any other suitable inflating means may be provided. For example, it is envisaged that the inflating means may be provided by syringes, which would be manually operated. It is also envisaged that a single inflating means may be provided, and where the device is provided with a primary and secondary balloon, the inflating means would be adapted to independently inflate and deflate the primary and secondary balloons. Independent inflating and deflating of the primary and secondary balloons would be achieved by providing a valving system between the single inflating means, be it a pump, a syringe or other such inflating means, and the primary and secondary balloons.

It is also envisaged that the primary balloon may be provided without primary stimulating and sensing electrodes, and in which case, any suitable inflating medium may be used for inflating the primary balloon, and the inflating means may be a liquid or gas, electrically conductive or non-electrically conductive.

It is also envisaged that where the secondary balloon is provided without secondary stimulating and sensing electrodes, the inflating medium may be a liquid or a gas.

While the gastric sleeve has been described as being formed in the stomach extending from the lower oesophageal sphincter to the antrum, it will be appreciated that in certain cases, the gastric sleeve may be formed in only a portion of the stomach between the lower oesophageal sphincter and the antrum, for example, it is envisaged that the gastric sleeve may extend from the lower oesophageal sphincter, but would terminate in the stomach at a location spaced apart from the antrum.

While it is desirable, it will be appreciated that it is not essential that the gastric sleeve be formed with a distal outwardly converging portion. In many cases, it is envisaged that the gastric sleeve may be formed to be of constant transverse cross-section along its entire length.

It will also of course be appreciated that while the former and the primary balloon are of circular transverse cross-section, and while the gastric sleeve will also be of substantially circular transverse cross-section when formed around the former or the primary balloon, as the case may be, while the former or the primary balloon is located within the gastric sleeve, once the former and/or the primary balloon have been removed from the gastric sleeve, it will be appreciated that the gastric sleeve will no longer be of circular transverse cross-section, since it will no longer have the support of the former or the primary balloon, as the case may be.

While the former and the primary balloon have been described as being of circular transverse cross-section, the former and the primary balloon, as well as the secondary balloon may be of any other suitable transverse cross-section.

The invention claimed is:

1. A method for monitoring the internal transverse cross-section of a gastric sleeve during formation thereof to a desired internal transverse cross-section in a subject in a sleeve gastrectomy, the method comprising:
providing a balloon catheter comprising a catheter having an elongated primary inflatable element located thereon and a secondary inflatable element located thereon and spaced apart distally from the primary inflatable element, the primary inflatable element when inflated having an elongated main cylindrical portion extending from a proximal end thereof to a distal portion of greater transverse cross-section than the transverse cross-section of the main cylindrical portion, and an intermediate portion located between the main cylindrical portion and the distal portion tapering proximally from the distal portion to the main cylindrical portion, the main cylindrical portion, the intermediate portion and the distal portion of the primary balloon being inflatable to transverse cross-sections similar to the desired internal transverse cross-sections to which the gastric sleeve is to be formed,
locating the primary inflatable element in the stomach of the subject with the secondary inflatable element located in the duodenum adjacent the pylorus with the pylorus located between the primary and secondary inflatable elements,
inflating the secondary inflatable element with the secondary inflatable element in engagement with the pylorus for correctly locating the primary inflatable element in the stomach to enable the gastric sleeve to be formed around the primary inflatable element,
inflating the primary inflatable element with an inflating medium so that the transverse cross-section of the distal portion of the primary inflatable element is greater than the transverse cross-section of the main cylindrical portion of the primary inflatable element, and the transverse cross-sections of the main cylindrical portion, the intermediate portion and the distal portion of the primary inflatable element approximate to the internal transverse cross-sections to which the gastric sleeve is to be formed,
urging the portion of the stomach which is to form the gastric sleeve around the inflated primary inflatable element,
suturing or stapling the stomach to form the gastric sleeve around the inflated primary inflatable element, and
monitoring one of a transverse cross-sectional area of the inflated primary inflatable element, a diameter of the inflated primary inflatable element and the pressure of the inflating medium in the inflated primary inflatable element during suturing or stapling of the stomach in order to produce the gastric sleeve of the desired transverse cross-section.

2. A method as claimed in claim 1 in which the pressure of the inflating medium in the primary inflatable element is monitored during suturing or stapling of the stomach in order to determine if the stomach is being excessively stretched around the primary inflatable element during suturing or stapling of the stomach.

3. A method as claimed in claim 1 in which the primary inflatable element is located in the stomach to extend from a location adjacent the lower oesophageal sphincter.

4. A method as claimed in claim 1 in which the primary inflatable element is located towards a distal end of a catheter, and the primary inflatable element on the catheter is entered orally into the stomach of the subject through the oesophagus.

5. A method as claimed in claim 1 in which a pair of axially spaced apart primary stimulating electrodes are located on the catheter within the primary inflatable element for receiving a primary stimulating signal, and a plurality of axially spaced apart primary sensing electrodes are located on the catheter between the primary stimulating electrodes and axially spaced apart therefrom, for producing a primary signal indicative of one of the transverse cross-sectional area and the diameter of the primary inflatable element in response to the primary stimulating signal when the primary inflatable element is inflated with an electrically conductive inflating medium, and a representation of the one of the transverse cross-sectional area and the diameter of the primary inflatable element adjacent each primary sensing electrode is displayed on a display means.

6. A method as claimed in claim 1 in which the primary inflatable element is inflated with a saline solution.

7. A method as claimed in claim 1 in which a former is placed in the stomach prior to forming the gastric sleeve around the primary inflatable element, and the gastric sleeve is formed around the former to a transverse cross-sectional area greater than the desired transverse cross-sectional area, and the stomach is sutured or stapled along a preliminary stapling line, and on completion of suturing or stapling the stomach along the preliminary stapling line, the former is removed and the primary inflatable element is inflated to the internal transverse cross-sectional area to which the gastric sleeve is to be formed, and the gastric sleeve is formed around the primary inflatable element.

8. A method as claimed in claim 1 in which the pressure of the inflating medium in the primary inflatable element is monitored as the portion of the stomach is being urged around the primary inflatable element.

9. A method as claimed in claim 1 in which the primary inflatable element extends into the antrum.

10. A method as claimed in claim 1 in which the primary inflatable element extends to a location adjacent the pylorus.

11. A method as claimed in claim 10 in which the pylorus is engaged by the primary and secondary inflatable elements.

12. A method as claimed in claim 5 in which the representations of the one of the transverse cross-sectional area and the diameter of the primary inflatable element adjacent each primary sensing electrode is displayed numerically on the display means.

13. A method as claimed in claim 5 in which a graphical representation of the primary inflatable element is displayed on the display means.

14. A method as claimed in claim 7 in which the former is an elongated hollow former.

15. A method as claimed in claim 7 in which the primary inflatable element is inserted into the stomach in the former.

* * * * *